United States Patent
Regmi et al.

(10) Patent No.: US 10,241,511 B2
(45) Date of Patent: Mar. 26, 2019

(54) EMERGENCY EVACUATION USING AUTONOMOUS DRIVING

(71) Applicant: Ford Global Technologies, LLC, Dearborn, MI (US)

(72) Inventors: Sagar Kumar Regmi, San Jose, CA (US); Shounak Athavale, San Jose, CA (US); Owen Carpenter, San Francisco, CA (US); Kevin Marx, Burlingame, CA (US); Srilaxmi Kanna, Burlingame, CA (US); Candice Xu, Mountain View, CA (US); Meiyappan Kannappa, Santa Clara, CA (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 85 days.

(21) Appl. No.: 15/342,527

(22) Filed: Nov. 3, 2016

(65) Prior Publication Data

US 2018/0120837 A1    May 3, 2018

(51) Int. Cl.
  *G05D 1/00* (2006.01)
  *A61B 5/01* (2006.01)
  (Continued)

(52) U.S. Cl.
  CPC ............ *G05D 1/0061* (2013.01); *A61B 5/01* (2013.01); *A61B 5/0205* (2013.01); *A61B 5/11* (2013.01);
  (Continued)

(58) Field of Classification Search
  CPC ...... G05D 1/0061; G05D 1/021; A61B 3/113; A61B 5/01; A61B 5/0205; A61B 5/11; A61B 5/18; B60K 28/06; B60K 28/066
  (Continued)

(56) References Cited

U.S. PATENT DOCUMENTS 6,946,966 B2    9/2005 Koenig
8,289,172 B2 *  10/2012 Matos .................... A62B 99/00
                                                              340/576
(Continued)

FOREIGN PATENT DOCUMENTS

DE    102017001996    11/2017
JP      2009163434     7/2009
WO   WO-2014015990 A1  1/2014

OTHER PUBLICATIONS

Ford car that can monitor your HEALTH as you drive and take over if you become ill or fall asleep, http://www.dailymail.co.uk/sciencetech/article2360694/FordcarmonitorHEALTHd.
(Continued)

*Primary Examiner* — Thomas G Black
*Assistant Examiner* — Luat T Huynh
(74) *Attorney, Agent, or Firm* — David R. Stevens; Stevens Law Group

(57) ABSTRACT

Methods and systems for detecting a medical emergency related to the driver of a vehicle are described. Various data, such as in-situ biophysical data of the driver, a medical history of the driver, and in-situ motion data of the vehicle, are employed to determine a possible medical emergency. In an event that a medical emergency is detected, the system determines the severity of the emergency and takes appropriate control of the vehicle. If the medical emergency is not life-threatening, the system may drive the vehicle to a safe area, park the vehicle, and then request help from emergency service providers (e.g., ambulance and police). If the medical emergency is severe (e.g., life-threatening), the system may transition the vehicle to an EMS (Emergency Medical Service)-privileged vehicle and autonomously drive the vehicle to an emergency service provider.

19 Claims, 5 Drawing Sheets

(51) Int. Cl.
*A61B 5/0205* (2006.01)
*A61B 5/11* (2006.01)
*A61B 5/18* (2006.01)
*B60K 28/06* (2006.01)
*B60R 1/00* (2006.01)
*G05D 1/02* (2006.01)
*A61B 3/113* (2006.01)
*A61B 5/00* (2006.01)
*A61B 5/021* (2006.01)
*A61B 5/024* (2006.01)
*A61B 5/08* (2006.01)

(52) U.S. Cl.
CPC ................ *A61B 5/18* (2013.01); *B60K 28/06* (2013.01); *B60K 28/066* (2013.01); *B60R 1/00* (2013.01); *G05D 1/021* (2013.01); *A61B 3/113* (2013.01); *A61B 5/0077* (2013.01); *A61B 5/021* (2013.01); *A61B 5/024* (2013.01); *A61B 5/0816* (2013.01); *B60R 2300/8006* (2013.01)

(58) Field of Classification Search
USPC ............................ 701/27; 340/436, 902–905
See application file for complete search history.

(56) References Cited

U.S. PATENT DOCUMENTS

| | | | |
|---|---|---|---|
| 8,874,301 B1 | 10/2014 | Rao | |
| 9,688,271 B2* | 6/2017 | Chan | B60W 30/025 |
| 2013/0018549 A1 | 1/2013 | Kobana et al. | |
| 2014/0074338 A1* | 3/2014 | Nordbruch | B60W 40/08 701/23 |
| 2014/0114356 A1 | 4/2014 | Couedic | |
| 2014/0135598 A1 | 5/2014 | Weidl | |
| 2014/0221781 A1* | 8/2014 | Schrauf | A61B 5/0205 600/301 |
| 2015/0246673 A1 | 9/2015 | Tseng | |
| 2016/0090055 A1 | 3/2016 | Breed | |
| 2017/0090476 A1* | 3/2017 | Letwin | G05D 1/0077 |
| 2018/0043901 A1* | 2/2018 | Kim | H04W 4/029 |
| 2018/0050696 A1* | 2/2018 | Misu | A61B 5/0077 |

OTHER PUBLICATIONS

The Potential for Adaptive Safety Through In-Vehicle Biomedical and Biometric Monitoring, Stephen A. Ridella, Julie J. Kang, Satoshi Kitazaki.

* cited by examiner

| Autonomous-driving mode 120 | Corresponding autonomous-driving level 140 | Narrative definition 160 |
|---|---|---|
| Mode A | High or 4 | Able to execute steering and acceleration/deceleration and drive the vehicle autonomously to a specific location |
| Mode B | Mid or 3 | Able to pull over the vehicle autonomously to a curbside or road shoulder |
| Mode C | Low or 2 | Able to decelerate the vehicle autonomously to a full stop |

FIG. 1

| AUTONOMOUS-DRIVING CLASSIFICATION OF A VEHICLE 220 | ALLOWED AUTONOMOUS-DRIVING MODE(S) 240 | ALLOWED AUTONOMOUS-DRIVING LEVEL(S) 260 |
|---|---|---|
| HIGH | A, B, C | 4, 3, 2 |
| MID | B, C | 3, 2 |
| LOW | C | 2 |
| NONE | NONE | NONE |

EMERGENCY EVACUATION USING AUTONOMOUS DRIVING

TECHNICAL FIELD

The present disclosure generally relates to autonomous driving and, more particularly, to methods and systems for safely evacuating a vehicle from traffic using autonomous driving, wherein the driver of the vehicle may be subject to a medical emergency.

BACKGROUND

For people who have certain medical conditions, there may be serious risks associated with driving a vehicle. For example, an epileptic may have a seizure while driving; and a diabetic may have a sudden drop in the blood glucose level, and thus lose consciousness, while driving. In general, older drivers, compared to younger drivers, tend to have a relatively higher chance of having a traffic incident due to medical emergencies. In case of such Sudden Medical Emergency (SME) incidents, the driver may lose control of the vehicle, thereby causing an uncontrollable traffic accident that may involve injuries or even casualties. Even for healthy drivers who are less likely to be subject to SME incidents, tiredness, drowsiness or fatigue due to prolonged driving and/or lack of rest may still result in temporary loss of focus and/or control of the vehicle. A split second of losing focus while driving, let alone losing control of the vehicle, may be enough to cause irreversible tragedy and forever remorse.

Even if an injury or casualty does not immediately occur in an SME incident where a driver of a vehicle loses control of the vehicle, in most occasions it remains dangerous to leave the vehicle in the traffic, or even in a driving lane, as an injury or casualty may possibly follow. For example, the driver may pass out due to an SME incident, and the uncontrolled vehicle may keep moving and eventually hit another vehicle or some roadside structure.

BRIEF DESCRIPTION OF THE DRAWINGS

Non-limiting and non-exhaustive embodiments of the present disclosure are described with reference to the following figures, wherein like reference numerals refer to like parts throughout the various figures unless otherwise specified.

FIG. 1 is a table listing a set of example autonomous-driving modes in accordance with an embodiment of the present disclosure.

FIG. 2 is a table listing a set of autonomous-driving classifications in accordance with an embodiment of the present disclosure.

DETAILED DESCRIPTION

Figure 3:
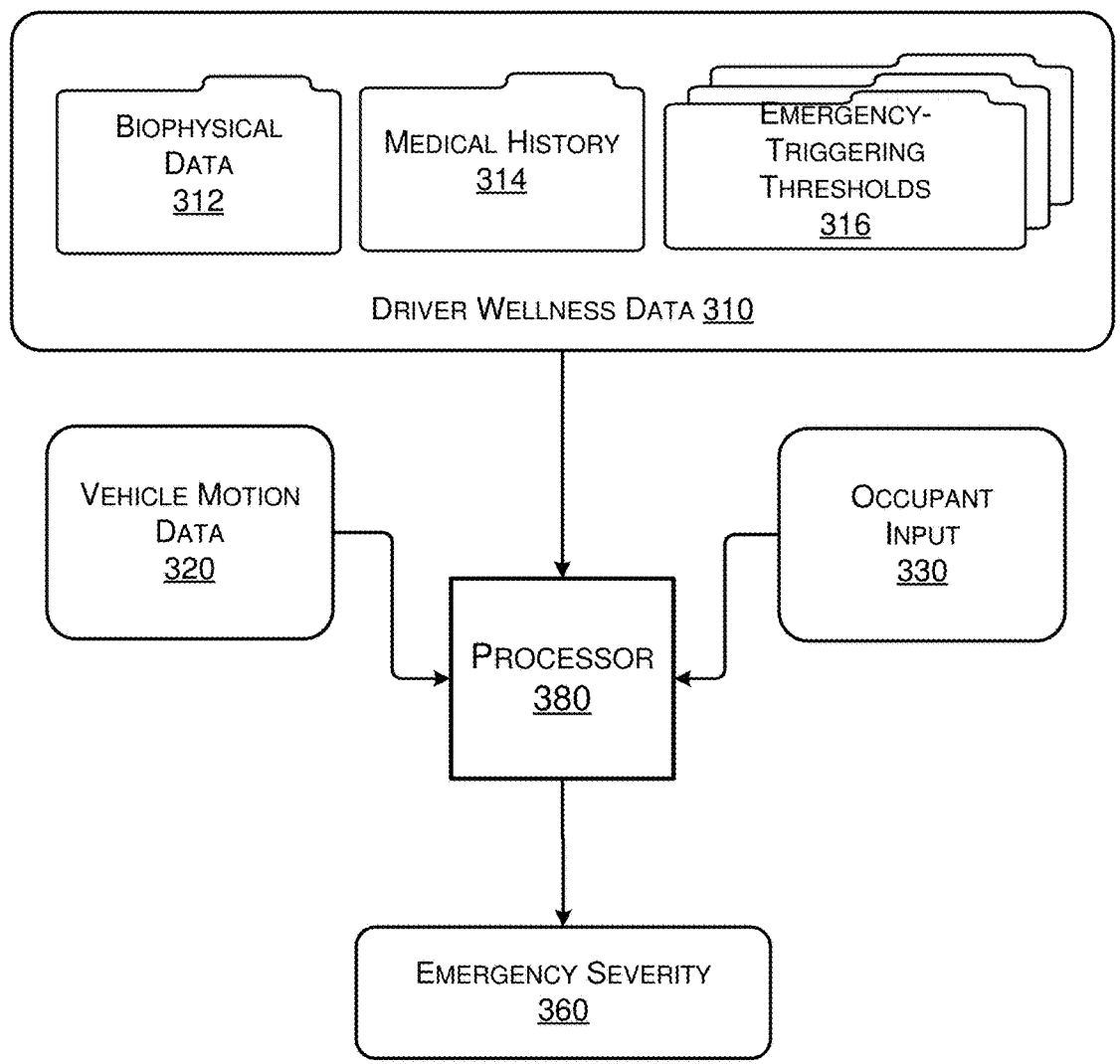
FIG. 3 is a diagram depicting a data flow for determining a severity level of a possible SME incident in accordance with an embodiment of the present disclosure.

In the following description, reference is made to the accompanying drawings that form a part thereof, and in which is shown by way of illustrating specific exemplary embodiments in which the disclosure may be practiced. These embodiments are described in sufficient detail to enable those skilled in the art to practice the concepts disclosed herein, and it is to be understood that modifications to the various disclosed embodiments may be made, and other embodiments may be utilized, without departing from the scope of the present disclosure. The following detailed description is, therefore, not to be taken in a limiting sense.

As automation technologies progress and become more mature, transportation vehicles, such as a car, a sedan, a truck, a passenger bus, or the like (hereinafter "a vehicle"), more vehicles are introduced to the market with various levels of "autonomous-driving" (i.e., autonomous driving) capabilities. The present disclosure aims to take preventive actions upon detecting a possible SME incident related to a driver of a vehicle moving in traffic. Specifically, autonomous-driving capabilities of the vehicle are engaged to autonomously evacuate the vehicle and the driver from the traffic, thereby reducing a risk of a traffic accident which might otherwise occur were the vehicle to stay in the traffic under little or no control of the driver due to the SME. A possible SME incident of the driver may be detected by monitoring various biophysical parameters of the driver while he or she is driving. Alternatively or additionally, a possible SME incident of the driver may be inferred by monitoring abnormal motions of the vehicle.

In various embodiments in accordance with the present disclosure, a vehicle may be capable of driving autonomously in one or more autonomous-driving modes. In FIG. 1, table 100 lists a set of autonomous-driving modes 120 (i.e., mode A, mode B and mode C) that may be incorporated in a vehicle. A respective narrative definition 160 is provided in table 100 for each autonomous-driving mode 120. In addition, each autonomous-driving mode 120 is associated with a corresponding autonomous-driving level 140. For example, mode A is associated with a high autonomous-driving level (or level 4), mode B is associated with a medium autonomous-driving level (or level 3), and mode C is associated with a low autonomous-driving level (or level 2). When operating in autonomous-driving mode A, the vehicle may be able to execute steering, acceleration and deceleration of the vehicle without any human intervention from the driver, thereby driving the vehicle to a specific location autonomously. When operating in autonomous-driving mode B, the vehicle may be able to autonomously pull itself over to a nearby safe location, such as a curbside or road shoulder, or into a parking lot located by the side of the traffic. When operating in autonomous-driving mode C, the vehicle may be able to decelerate autonomously, without any driver intervention, until the vehicle comes to a full stop.

A vehicle, upon being manufactured, may be classified with a certain autonomous-driving classification. In FIG. 2, table 200 lists several autonomous-driving classifications 220, such as "high", "mid", "low" and "none". A vehicle may, depending on its autonomous-driving capabilities as designed or allowed, be classified as either one of the classifications 220. Each autonomous-driving classification 220 may be configured to operate in none, one or more autonomous-driving modes 240, with each autonomous-driving mode 240 denoted with an autonomous-driving level 260 in the same way as shown in table 100. For example, if a vehicle is classified with a "high" autonomous-driving classification, the vehicle is able and allowed to operate in autonomous-driving mode A (denoted by autonomous-driving level 4, or level 4), mode B (denoted by autonomous-driving level 3, or level 3) and mode C (denoted by autonomous-driving level 2, or level 2). If a vehicle is classified with a "mid" autonomous-driving classification, the vehicle is able and allowed to operate in autonomous-driving mode B (level 3) and mode C (level 2), but not in autonomous-driving mode A (level 4). Likewise, if a vehicle is classified with a "low" autonomous-driving classification, the vehicle is able and allowed to operate in autonomous-driving mode C (level 2), but not in autonomous-driving mode A level 4) or mode B (level 3). In addition, there may be vehicles that are not designed with, or allowed for, any autonomous driving. Such vehicles are thus classified with a "none" autonomous-driving classification, and not allowed to operate in any autonomous-driving mode.

Various information may be analyzed or otherwise utilized to determine whether a driver of a vehicle may be subject to a SME incident. Specifically, a figure of merit, "emergency severity", is to be determined based on the various information regarding a potential SME incident of the driver. FIG. 3 depicts a data flow that includes various factors or types of information for determining a severity level of a possible SME incident. A processor 380 may determine an emergency severity 360 using information such as driver wellness data 310, vehicle motion data 320, and/or input 330 from an occupant of the vehicle (i.e., either the driver of the vehicle or a passenger in the vehicle). Depending on how severe the possible SME may be, as indicated by emergency severity 360, processor 380 may further determine an evacuation plan to autonomously evacuate the vehicle, along with any occupant in the vehicle, from the traffic.

Figure 4:
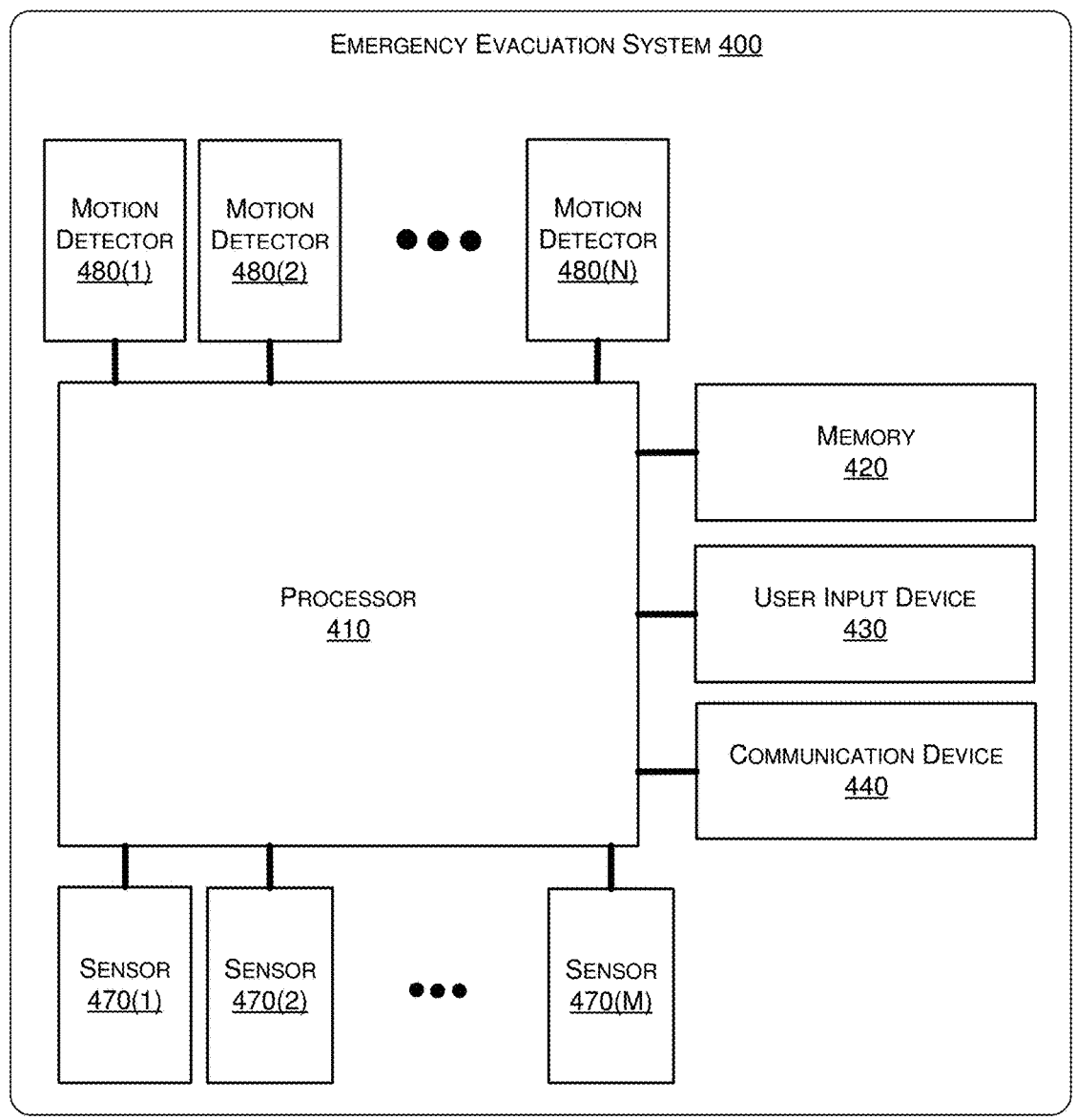
FIG. 4 is a block diagram depicting an example apparatus in accordance with an embodiment of the present disclosure.

FIG. 4 illustrates an example apparatus, or emergency evacuation system 400, in accordance with an embodiment of the present disclosure. Emergency evacuation system 400 may perform various functions related to techniques, methods and systems described herein, including those described above with respect to autonomous-driving modes 120 listed in table 100, and the determining of emergency severity 360, as well as those described below with respect to process 500. Emergency evacuation system 400 may be installed, equipped or otherwise implemented in a vehicle that has an autonomous-driving classification 220 of "high", "mid" or "low" as listed in table 200 to effect various embodiments in accordance with the present disclosure. Emergency evacuation system 400 may include at least some of the components illustrated in FIG. 4.

Referring to FIG. 3 and FIG. 4, processor 410 may be an example implementation of processor 380. Processor 410 may be implemented in the form of one or more integrated-circuit (IC) chips and any supporting electronics, and may be installed in a control console of a vehicle. Processor 410 may be communicatively connected to various operational components of the vehicle to control or otherwise maneuver the vehicle to autonomously drive the vehicle in accordance with the present disclosure.

In some embodiments, emergency evacuation system 400 may include one or more sensors 470(1)-470(M), where M is a positive integer greater than or equal to 1. The one or more sensors 470(1)-470(M) may be configured to detect one or more biophysical parameters of a driver of a vehicle, as described above. For instance, the one or more sensors 470(1)-470(M) may detect one or more of a heart rate reading, a blood pressure reading, a body temperature reading, a respiration reading, a body movement, an eye movement, and a facial distortion of the driver.

In some embodiments, emergency evacuation system 400 may also include one or more motion detectors 480(1)-480(N), where N is a positive integer greater than or equal to 1. The one or more motion detectors 480(1)-480(N) may be configured to detect one or more motion parameters of the vehicle, as described above. For instance, the one or more motion detectors 480(1)-480(N) may detect one or more of a speed of the vehicle, a moving direction of the vehicle, and a distance between the vehicle and a nearby object.

In some embodiments, emergency evacuation system 400 may include a user input device 430 configured to receive one or more user inputs from a user (i.e., an occupant) of the vehicle, as described above. With user input device 430, an occupant of the vehicle may instruct emergency evacuation system 400 to engage the vehicle into one of the autonomous-driving modes 120 to evacuate the vehicle from traffic autonomously.

In some embodiments, emergency evacuation system 400 may include a communication device 440 configured to wirelessly transmit and receive data. In some embodiments, communication device 440 may be configured to receive medical history 314 and/or emergency-triggering thresholds 316 as part of driver wellness data 310. In some embodiments, communication device 440 may be configured to transmit biophysical data 312 collected by sensors 470(1)-470(M) and/or vehicle motion data 320 collected by motion detectors 480(1)-480(N) to an emergency service, a hospital, an ambulance, or a police department.

In some embodiments, emergency evacuation system 400 may further include one or more processors, such as a processor 410, coupled to receive data on the one or more parameters from the one or more sensors 470(1)-470(M) and one or more motion detectors 480(1)-480(N). In addition, the one or more processors may be further coupled to receive the one or more user inputs from the user input device 430, as well as data from communication device 440. Processor 410 may receive wellness data 310 of the driver. Processor 410 may also determine an emergency severity 360 based on the wellness data 310. Processor 410 may further determine an evacuation plan based on the emergency severity and an autonomous-driving classification (such as autonomous-driving classification 220) of the vehicle. Processor 410 may also execute the evacuation plan such that the vehicle and the driver are evacuated from traffic with autonomous driving.

Emergency evacuation system 400 may include a memory device 420 coupled to processor 410. Memory device 420 may be configured to store data, firmware and software programs therein. For example, memory device 420 may store wellness data 310 of the driver, which may include biophysical data 312, medical history 314, and/or a set of emergency-triggering thresholds 316 of the driver.

In some embodiments, driver wellness data 310 may include biophysical data 312 of the driver. In some embodiments, biophysical data 312 of the driver may be collected or otherwise monitored through one or more biophysical sensors, such as sensors 470(1)-470(M) in an emergency evacuation system 400 implementable in a vehicle, as shown in FIG. 4. Sensors 470(1)-470(M) may be disposed at various locations in or on the vehicle. In some embodiments, sensors 470(1)-470(M) may be in contact with or worn by the driver to monitor or collect biophysical data 312. For example, sensor 470(1) may be a heart rate sensor disposed on a seatbelt of the vehicle, and configured to provide a heart rate reading of the heart rate of the driver as biophysical data 312 when the seatbelt is engaged with or worn by the driver. As another example, sensor 470(2) may be a blood pressure sensor disposed on an armrest of a driver's seat of the vehicle, and configured to provide a blood pressure reading of the blood pressure of the driver as biophysical data 312 when the driver places his or her arm on the armrest while driving. Likewise, sensors 470(1)-470(M) may include a thermometer, a respiratory rate monitor, a blood glucose monitor, or the like, to provide biophysical data 312 of the driver, such as a body temperature reading, a respiration reading, a blood glucose reading, or the like. In some embodiments, sensors 470(1)-470(M) may include a video camera or an infrared image sensor to capture video(s) and/or image(s) of the driver and provide imagery data indicative of a body movement, an eye movement, or a facial distortion of the driver as biophysical data 312. Using facial detection or other image processing techniques, a processor 410 may analyze the video(s) or image(s) and accordingly determine emergency severity 360 for a potential SME. For example, sensors 470(1)-470(M) may include a video camera, and processor 410 may analyze a video received from the video camera and find that the driver may have passed out in the driver's seat. Processor 410 may determine this condition to be very likely a SME incident, of which the emergency severity 360 may be "life-threating".

In some embodiments, driver wellness data 310 of the driver may also include a medical history 314 of the driver, and/or a set of emergency-triggering thresholds 316 of the driver, as shown in FIG. 3. Medical history 314 may include information on one or more pre-existing medical condition(s) of the driver, such as hypertension or diabetes for example. Medical history 314 of the driver may be transmitted from a remote location, such as a cloud server of a medical service provider, and received by emergency evacuation system 400 through communication device 440 thereof. Alternatively, medical history 314 of the driver may be readily stored in memory 420 of emergency evacuation system 400. Processor 380 of FIG. 3, or equivalently, processor 410 of FIG. 4, may analyze the medical history 314 of the driver while determining emergency severity 360. For example, processor 410 may analyze medical history 314 and find that the driver is a diabetic, and thus may monitor a blood glucose reading of biophysical data 312, received from a blood glucose sensor among sensors 470(1)-470(M). In some embodiments, driver wellness data 310 of the driver may include a set of emergency-triggering thresholds 316 associated with the specific driver, which may be provided by a medical doctor or medical service provider. For example, in the case of the diabetic driver, the set of emergency-triggering thresholds 316 may include a "life-threatening" low-bound blood glucose threshold of 80 mg/dl (milligram per deciliter), and a "non-life-threatening" low-bound blood glucose threshold of 100 mg/dl, as dictated by a medical service provider. In this example, processor 410 may determine that there is no potential SME incident should the blood glucose sensor reports a reading higher than 100 mg/dl. Moreover, processor 410 may determine that there is a potential SME incident of "life-threating" severity should the blood glucose sensor reports a reading lower than 80 mg/dl. Furthermore, processor 410 may determine that there is a potential SME incident of "less-than-life-threating" severity should the blood glucose sensor reports a reading between 80 mg/dl and 100 mg/dl.

Additionally or alternatively, in some embodiments, processor 380 of FIG. 3, or equivalently, processor 410 of FIG. 4, may determine emergency severity 360 based on vehicle motion data 320. The vehicle motion data 320 may include various motion parameters of the vehicle, such as a speed of the vehicle, a moving direction of the vehicle, and/or a distance between the vehicle and a nearby object. Vehicle motion data 320 of the vehicle may be collected or otherwise monitored through one or more motion detectors disposed in or on the vehicle, such as motion detectors 480(1)-480(N) of emergency evacuation system 400 of FIG. 4. The motion detectors 480(1)-480(N) may include one or more of a speedometer, a global positioning device, a video camera, and a proximity sensor. For example and without limitation, processor 410 may find that the vehicle is neither slowing down nor staying in a driving lane at a bend of a road, but rather going straight at the bend toward a side edge of the road. With an anticipation of the vehicle colliding with a roadside structure within seconds, processor 410 may determine that there is a potential SME incident with the driver of "life-threating" severity.

Additionally or alternatively, processor 380 of FIG. 3, or equivalently, processor 410 of FIG. 4, may determine emergency severity 360 based on a human input 330 of an occupant of the vehicle. The occupant may be either the driver of the vehicle or a passenger riding in the vehicle. The occupant input 330 may be received by processor 380/processor 410 via a user interface, such as user input device 430 of emergency evacuation system 400 of FIG. 4. The user input device 430 may be, for example and without limitation, a "panic" button located on a steering wheel of the vehicle, or a touch screen located on a dashboard of the vehicle. Alternatively or additionally, user input device 430 may be a voice-activating interface that is configured to receive a voice command from an occupant of the vehicle. For example, a driver having a medical history of hypertension may feel his or her vision become blurry, and may instruct emergency evacuation system 400 through a voice command to pull over to the side of the road. As another example, an epileptic school bus driver may have a seizure while driving, losing control of the vehicle. A passenger may press a panic button on the dashboard to indicate that a life-threatening SME incident may have happened, and emergency evacuation system 400 may engage the school bus into a high autonomous-driving mode and autonomously maneuver the school bus to a nearby hospital with emergency room.

In some embodiments, in determining the evacuation plan, processor 410 may be configured to determine a set of autonomous-driving modes (such as autonomous-driving modes 120) allowed by the autonomous-driving classification of the vehicle. Each of the autonomous-driving modes may have a respectively different autonomous-driving level (such as autonomous-driving level 140). In executing the evacuation plan, processor 410 may attempt to execute the set of autonomous-driving modes in a descending order of the autonomous-driving levels until one of the set of autonomous-driving modes is executed successfully.

In some embodiments, in executing an autonomous-driving mode that has a high autonomous-driving level, processor 410 may drive the vehicle autonomously to an emergency room, a hospital, an ambulance, or an emergency medical service (EMS) vehicle. In some embodiments, in executing an autonomous-driving mode that has a middle autonomous-driving level, processor 410 may drive the vehicle autonomously to a safe location in a vicinity of the vehicle, such as a side of a road, a shoulder of the road, or a parking lot by the road. In some embodiments, in executing an autonomous-driving mode that has a low autonomous-driving level, processor 410 may reduce a speed of the vehicle autonomously until the vehicle fully stops.

In some embodiments, processor 410 may be configured to perform additional operations. For example, processor 410 may turn on emergency lighting of the vehicle so as to warn surrounding vehicles about the potential SME incident or otherwise make the vehicle identified by the surrounding vehicles. As another example, processor 410 may notify an emergency service regarding a condition of the driver, the vehicle, or both.

Additionally or alternatively, processor 410 may be configured to perform further operations. For example, processor 410 may place a request for a crowd-sourced emergency response to other vehicles or individuals that happen to be in the region where the vehicle is located. As another example, processor 410 may continually monitor the wellness data of the driver, and transmit the wellness data to an emergency service, a hospital, an ambulance, or a police department.

Figure 5:
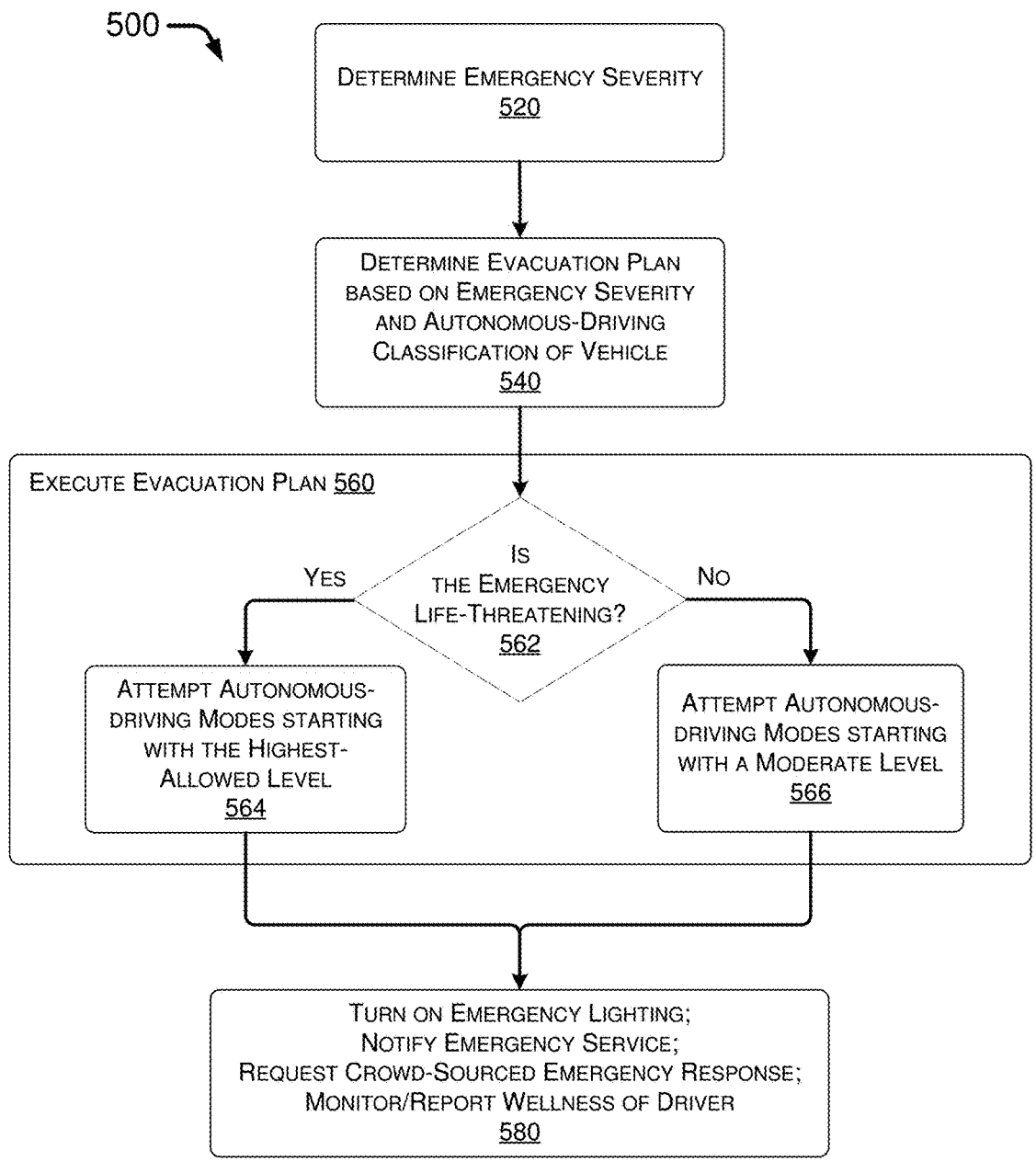
FIG. 5 is a flowchart depicting an example process in accordance with an embodiment of the present disclosure.

FIG. 5 illustrates an example process 500, in accordance with the present disclosure, for evacuating a vehicle from traffic upon determining a driver of the vehicle may be subject to a SME incident. Process 500 may include one or more operations, actions, or functions shown as blocks such as 520, 540, 560 and 580 as well as sub-blocks 562, 564 and 566. Although illustrated as discrete blocks, various blocks of process 500 may be divided into additional blocks, combined into fewer blocks, or eliminated, depending on the desired implementation. Process 500 may be implemented by emergency evacuation system 400. In addition, process 500 may use the data flow depicted in FIG. 3 in determining an emergency severity for a potential SME incident. Process 500 may begin with block 520.

At 520, process 500 may involve processor 410 determining emergency severity 360 based on driver wellness data 310. Referring to various examples mentioned above, processor 410 may determine emergency severity 360 of a potential SME incident to be either "life-threatening" or "less-than-life-threatening" based on one or more of driver wellness data 310, vehicle motion data 320, and occupant input 330. Process 500 may proceed from 520 to 540.

At 540, process 500 may involve processor 410 determining an evacuation plan based on the emergency severity 360 and an autonomous-driving classification of the vehicle (such as autonomous-driving classification 220). For instance, in the example of the epileptic school bus driver discussed above, in the event that the blood glucose reading is higher than 100 mg/dl, processor 410 may determine that emergency severity 360 is so low that there is not a SME incident happening, and subsequently determines that an evacuation plan is not needed. Alternatively, in the event that the blood glucose reading is lower than 100 mg/dl, processor 410 may determine that emergency severity 360 is high enough to identify a SME incident being taking place, and subsequently determines an evacuation plan. The evacuation plan may include a set of autonomous-driving modes (such as autonomous-driving modes 120) allowed by the autonomous-driving classification of the vehicle. For instance, in the example of the epileptic school bus driver, the school bus may have a "high" autonomous-driving classification, which allows the school bus to operate in all of modes A, B and C according to table 200. In dealing with the SME incident, processor 410 may determine an evacuation plan that includes three possible operation modes for the vehicle, namely, an autonomous-driving mode A, an autonomous-driving mode B, and an autonomous-driving mode C. When operated in autonomous-driving mode A, emergency evacuation system 400 may command the vehicle to autonomously drive to an emergency room, a hospital, an ambulance, or an EMS vehicle. When operated in autonomous-driving mode B, emergency evacuation system 400 may command the vehicle to autonomously pull over to a safe location in a vicinity of the vehicle, such as a side of a road, a shoulder of the road, or a parking lot by the road. When operated in autonomous-driving mode C, emergency evacuation system 400 may command the vehicle to autonomously reduce the speed of the vehicle until the vehicle fully stops. Each of autonomous-driving modes A, B and C has a respectively different autonomous-driving level (such as autonomous-driving level 140 of table 100) to denote an autonomous-driving level required to operate the vehicle in the respective autonomous-driving mode. Process 500 may proceed from 540 to 560.

At 560, process 500 may involve processor 410 executing the evacuation plan such that the vehicle and the driver are evacuated from the traffic with autonomous driving. In some embodiments, the executing of the evacuation plan may involve processor 410 attempting to execute the set of autonomous-driving modes in a descending order of the autonomous-driving levels until one of the set of autonomous-driving modes is executed successfully. For instance, in the example of the epileptic school bus driver, processor 410 may attempt to start driving the school bus in autonomous-driving mode A, which has a corresponding autonomous-driving level of 4, according to table 100. In an event that the school bus successfully drives to a nearby hospital autonomously, process 500 may end at 560. However, there may be situations in which the school bus fails to drive to a nearby hospital autonomously. For example, a closest hospital may be 20 miles away, but the gas tank of the school bus holds only 3 gallons of gasoline, which is not enough to drive to the hospital. In such an event that the vehicle fails to execute the evacuation plan according to mode A, processor 410 may subsequently attempt to drive the vehicle with an autonomous-driving mode having the next highest autonomous-driving level, which is autonomous-driving mode B (having autonomous-driving level of 3). Namely, processor 410 may attempt to pull over the school bus to a shoulder of the road. In an event that the school bus successfully pull over to the road shoulder autonomously, process 500 may end at 560. However, there may be situations in which the school bus fails to pull over to the road shoulder or a side of the road. For example, the school bus may be driving in an inner lane of road, while the outer lane is occupied by other vehicles which do not allow the school bus to change lane to the outer lane for pulling over. In such an event that the vehicle also fails to execute the evacuation plan according to mode B, processor 410 may subsequently attempt to drive the vehicle with an autonomous-driving mode having the next highest autonomous-driving level, which is autonomous-driving mode C (having autonomous-driving level of 2). Namely, while maintaining the school bus in the inner lane, processor 410 may attempt to slow down the school bus autonomously until the school bus is fully stopped in the inner lane.

In some embodiments, the executing of the evacuation plan may involve processor 410 attempting to operate the vehicle for either the whole set of the autonomous-driving modes, or a subset of the autonomous-driving modes, based on the emergency severity 360. Specifically, at 560, process 500 may involve processor 410 performing a number of operations, as shown in sub-blocks 562, 564 and 566. At 562, process 500 may involve processor 410 identifying, based on emergency severity 360, whether the SME incident is life-threatening or not. In an event that processor 410 identifies the SME incident to be life-threatening, process 500 may proceed from 562 to 564. Alternatively, in an event that processor 410 identifies the SME incident to be non-life-threatening, process 500 may proceed from 562 to 566. At 564, processor 410 attempts to operate each of the set of autonomous-driving modes, starting from a mode having the highest-allowed autonomous-driving level. That is, process 500 involves processor 410 attempting to operate the vehicle starting from an autonomous-driving mode that has the highest autonomous-driving level allowed by the autonomous-driving classification of the vehicle. Alternatively, at 566, processor 410 only attempts to operate a subset of the set of autonomous-driving modes, starting from a mode with a moderate autonomous-driving level. That is, process 500 involves processor 410 attempting to operate the vehicle starting from a moderate autonomous-driving level. For instance, in the example of the epileptic school bus driver discussed above, in an event that the blood glucose reading is lower than the life-threatening low threshold of 80 mg/dl, processor 410 would identify the SME to be "life-threatening", and execute the set of autonomous-driving modes of the evacuation plan starting from mode A in a descending order of the autonomous-driving levels until one autonomous-driving mode is executed successfully. Alternatively, in the event that the blood glucose reading is higher than the life-threatening low threshold of 80 mg/dl but still lower than the non-life-threatening low threshold of 100 mg/dl, processor 410 would then identify the SME to be "non-life-threatening", and execute the set of autonomous-driving modes of the evacuation plan in a descending order of the autonomous-driving levels starting from a moderate level, such as mode B, until one autonomous-driving mode is executed successfully. Process 500 may proceed from 564 to 580. Process 500 may also proceed from 566 to 580.

In some embodiments, with the vehicle having a "high" autonomous-driving classification, the highest autonomous-driving mode allowed by the "high" autonomous-driving classification may include acquiring or otherwise obtaining an EMS privilege for the vehicle and driving the vehicle autonomously as an EMS-privileged vehicle. For instance, in the example of the epileptic school bus driver discussed above, when operating in autonomous-driving mode A, processor 410 may make a request to the police department or emergency service department to acquire an EMS privilege. With the EMS privilege granted, the school bus may now be identified as an EMS-privileged vehicle (i.e., a vehicle having an EMS status), and may drive to the hospital autonomously as an EMS vehicle, just like an ambulance or a police car. Processor 410 may make the request for, and receive a grant of, the EMS privilege through communication device 440. In some embodiments, after the EMS privilege has been acquired, processor 410 may further notify nearby vehicles about the EMS status using a vehicle-to-vehicle (V2V) communication technology. The nearby vehicles may thus give a right-of-way to the EMS-privileged vehicle such that the vehicle may evacuate from the traffic efficiently and effectively. Likewise, the V2V notification of the EMS status may be realized through communication device 440.

In some embodiments, a vehicle having the EMS status may have higher "priority" compared to other vehicles in the traffic that do not have the EMS status. That is, upon being notified of the EMS status via the V2V notification, autonomous vehicles without the EMS status and nearby a vehicle having the EMS status may yield to the vehicle having the EMS status. This may aid the vehicle having the EMS status in reaching its destination (e.g., an emergency service, a hospital, an ambulance, or a police department).

In some embodiments, with the vehicle having a "high" autonomous-driving classification, the highest autonomous-driving mode allowed by the "high" autonomous-driving classification may include determining a most suitable destination for the vehicle such that a SME may be best dealt with. The most suitable destination may be either a fixed medical facility such as a hospital, or mobile medical facility such as an ambulance. The most suitable destination may be determined by a distance of a medical facility from the vehicle, or by a period of time within which a medical facility may be able to meet with the vehicle. The determining of the most suitable destination may involve processor 410 executing a software algorithm stored in memory 420 to calculate the distance or to estimate the period of time, or both. For instance, in the example of the epileptic school bus driver discussed above, when operating in autonomous-driving mode A, processor 410 may calculate the nearest hospital is 10 miles away from a current location of the school bus, while an ambulance is moving in a street that is 5 miles away from the current location of the school bus. Accordingly, processor 410 may determine the ambulance to be the most suitable destination for the evacuation plan, given that the ambulance is closer to the current location of the vehicle than the hospital. Alternatively, processor 410 may estimate a period of time within which the school bus may arrive at either medical facility, considering a condition of the traffic. For instance, processor 410 may estimate it would take 10 minutes to arrive at the hospital that is 10 miles away, as the school bus may autonomously drive to the hospital along a freeway that has very light traffic for the time being. However, processor 410 may estimate it would take 15 minutes to arrive at the ambulance that is 5 miles away, as the school bus has to autonomously drive to the ambulance on a surface road that is currently having heavy traffic in a direction from the school bus to the ambulance. Accordingly, processor 410 may determine the hospital to be the most suitable destination for the evacuation plan, given that the school bus may be able to arrive at the hospital within a shorter period of time, even though the hospital is located farther away than the ambulance. In some embodiments, the vehicle may contact a mobile medical facility using the V2V communication technology to shorten the period of time within which the vehicle may arrive at the mobile medical facility. For instance, such that the ambulance may also move toward the school bus while the school bus moves toward the ambulance. For instance, in the example of the epileptic school bus driver discussed above, when operating in autonomous-driving mode A, processor 410 may communicate with the ambulance using V2V communication through communication device 440 such that the ambulance and the school bus move toward one another simultaneously. The ambulance and the school bus may thus meet in a middle location (i.e., meet half-way) to save critical time. Consequently, the time within which the school bus may arrive at the ambulance may be reduced to only 5 minutes, as the surface road has light traffic in a direction from the ambulance to the school bus. Accordingly, processor 410 may determine the evacuation plan as meeting the ambulance at the middle location, and thus the ambulance to be the most suitable destination for the evacuation plan. In some embodiments, any suitable communication technology, including V2V communication, mobile communication, Internet and cloud, may be utilized between a vehicle in need of help and another vehicle (e.g., ambulance) to exchange vehicle information (e.g., make and model of the car, license plate number, color of car and the like) to aid the ambulance in identifying the vehicle in need of help.

In some embodiments, with the vehicle having a "high" autonomous-driving classification, the highest autonomous-driving mode allowed by the "high" autonomous-driving classification may include acquiring a platooning escort for the vehicle and driving the vehicle autonomously with the platooning escort. For instance, in the example of the epileptic school bus driver discussed above, when operating in autonomous-driving mode A, processor 410 may make a request to the police department or emergency service department for receiving a platooning escort. A police car may provide the platooning escort by leading the school bus to its destination (such as a hospital). The school bus may follow the police car (i.e., "platoon" with the police car) autonomously to the hospital. Process 500 may proceed from 560 to 580.

At 580, process 500 may involve processor 410 performing one or more of other operations. Specifically, process 500 may involve processor 410 turning on various emergency lighting equipped on the vehicle, such that other vehicles in the traffic may be aware that the vehicle may be in the process of emergency evacuation through autonomous-driving. In some embodiments, process 500 may involve processor 410 notifying the emergency service provider regarding a condition of the driver, the vehicle, or both, so that the emergency service provider, such as an emergency room of a hospital, may be prepared to take over the driver once he or she arrives at the hospital via autonomous-driving. In some embodiments, process 500 may involve processor 410 requesting a crowd-sourced emergency response to other vehicles in a vicinity of the vehicle. Some off-duty officer or medical doctor may happen to be in the area, and would be able to attend to the needs of the driver earlier than the vehicle arrives at the hospital autonomously. In some embodiments, process 500 may involve processor 410 continually monitoring the wellness data of the driver and transmitting the wellness data to an emergency service, a hospital, an ambulance, or a police department.

The present disclosure provides convenient, reliable, versatile and well-rounded systems and methods for detecting a possible Sudden Medical Emergency a driver of an automobile vehicle may be subject to, and subsequently execute an evacuation plan to evacuate the automobile vehicle, the driver, along with other passengers in the vehicle, to safety using autonomous driving. The evacuation plan may be different according to the severity of the emergency, as well as the autonomous-driving classification of the vehicle. If the medical emergency is decided not life-threatening, the system may drive the vehicle to a safe area, park the vehicle, and the request help from emergency service providers (e.g., ambulance and police). If the medical emergency is severe (e.g., life-threatening), the system may transition the vehicle to an EMS-privileged vehicle and autonomous drive the vehicle to a hospital or an emergency service provider.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors, and may include hardware logic/electrical circuitry controlled by the computer code. These example devices are provided herein purposes of illustration, and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

The invention claimed is:

1. A method, comprising:
receiving, by a processor, wellness data of a driver driving a vehicle in traffic;
determining, by the processor, an emergency severity based on the wellness data;
determining, by the processor, an evacuation plan based on the emergency severity and an autonomous-driving classification of the vehicle; and
executing, by the processor, the evacuation plan such that the vehicle and the driver are evacuated from the traffic with autonomous driving,
wherein:
the evacuation plan comprises a set of autonomous-driving modes allowed by the autonomous-driving classification of the vehicle, each of the autonomous-driving modes having a respectively different autonomous-driving level, the set of autonomous-driving modes comprising a highest autonomous-driving mode having a highest autonomous-driving level among the set of autonomous-driving modes,
in an event that the emergency severity is determined to be life-threatening, the execution of the evacuation plan comprises attempting to execute the set of autonomous-driving modes in a descending order of the autonomous-driving levels until one of the set of autonomous-driving modes is executed successfully, and
in an event that the emergency severity is determined to be less than life-threatening, the execution of the evacuation plan comprises attempting to execute at least a subset of the autonomous-driving modes in a descending order of the autonomous-driving levels until one of the subset of the autonomous-driving modes is executed successfully.

2. The method of claim 1, wherein:
the receiving of the wellness data of the driver comprises receiving the wellness data from a set of sensors disposed in or on the vehicle, or worn by the driver,
the set of sensors comprises one or more of a heart rate sensor, a blood pressure sensor, a thermometer, a respiratory rate monitor, a video camera, and an infrared image sensor, and
the wellness data comprises a set of biophysical data comprising one or more of a heart rate reading, a blood pressure reading, a body temperature reading, a respiration reading, a body movement, an eye movement, and a facial distortion.

3. The method of claim 2, wherein:
the wellness data further comprises a medical history, a set of emergency-triggering thresholds, or both, associated with the driver, and
the determining of the emergency severity comprises comparing the set of biophysical data to the medical history or the set of emergency-triggering thresholds.

4. The method of claim 1, further comprising:
receiving, by the processor, motion data of the vehicle,
wherein the determining of the emergency severity further comprises determining the emergency severity based on the motion data.

5. The method of claim 1, further comprising:
receiving, by the processor, a human input from an occupant of the vehicle,
wherein the determining of the emergency severity further comprises determining the emergency severity based on the human input.

6. The method of claim 1, wherein the autonomous-driving classification of the vehicle is a high classification, and wherein the highest autonomous-driving mode allowed by the high classification comprises driving the vehicle autonomously to an emergency room, a hospital, an ambulance, or an emergency medical service (EMS) vehicle.

7. The method of claim 6, wherein the highest autonomous-driving mode allowed by the high classification further comprises at least one of the following:

acquiring an EMS privilege for the vehicle and driving the vehicle autonomously as an EMS-privileged vehicle; and acquiring a platooning escort and driving the vehicle autonomously with the platooning escort.

8. The method of claim 1, wherein the autonomous-driving classification of the vehicle is a middle classification, and wherein the highest autonomous-driving mode allowed by the middle classification comprises driving the vehicle autonomously to a safe location in a vicinity of the vehicle, the safe location comprising a side of a road, a shoulder of the road, or a parking lot by the road.

9. The method of claim 1, wherein the autonomous-driving classification of the vehicle is a low classification, and wherein the highest autonomous-driving mode allowed by the low classification comprises reducing a speed of the vehicle autonomously until the vehicle fully stops.

10. The method of claim 1, further comprising at least one of the following:
turning on emergency lighting of the vehicle;
notifying an emergency service regarding a condition of the driver, the vehicle, or both;
requesting a crowd-sourced emergency response to other vehicles in a vicinity of the vehicle; and
continually monitoring the wellness data of the driver and transmitting the wellness data to an emergency service, a hospital, an ambulance, or a police department.

11. An emergency evacuation system implementable in a vehicle, comprising:
a memory configured to store one or more sets of instructions; and
a processor coupled to execute the one or more sets of instructions stored in the memory, the processor, upon executing the one or more sets of instructions, configured to perform operations comprising:
receiving wellness data of a driver;
receiving motion data of the vehicle;
determining an emergency severity based on the wellness data and the motion data;
determining an evacuation plan based on the emergency severity and an autonomous-driving classification of the vehicle; and
executing the evacuation plan such that the vehicle and the driver are evacuated from traffic with autonomous driving,
wherein:
the evacuation plan comprises a set of autonomous-driving modes allowed by the autonomous-driving classification of the vehicle, each of the autonomous-driving modes having a respectively different autonomous-driving level, the set of autonomous-driving modes comprising a highest autonomous-driving mode having a highest autonomous-driving level among the set of autonomous-driving modes,
in an event that the emergency severity is determined to be life-threatening, the execution of the evacuation plan comprises attempting to execute the set of autonomous-driving modes in a descending order of the autonomous-driving levels until one of the set of autonomous-driving modes is executed successfully, and
in an event that the emergency severity is determined to be less than life-threatening, the execution of the evacuation plan comprises attempting to execute at least a subset of the autonomous-driving modes in a descending order of the autonomous-driving levels until one of the subset of the autonomous-driving modes is executed successfully.

12. The emergency evacuation system of claim 11, further comprising:
a set of biophysical sensors disposed in or on the vehicle, or worn by the driver, the set of biophysical sensors comprising one or more of a heart rate sensor, a blood pressure sensor, a thermometer, a respiratory rate monitor, a video camera, and an infrared image sensor,
wherein the wellness data of the driver comprises a set of biophysical data comprising one or more of a heart rate reading, a blood pressure reading, a body temperature reading, a respiration reading, a body movement, an eye movement, and a facial distortion, and
wherein, in receiving the wellness data of the driver, the processor is configured to receive the wellness data from the set of biophysical sensors.

13. The emergency evacuation system of claim 12, wherein:
the wellness data further comprises a medical history, a set of emergency-triggering thresholds, or both, associated with the driver, and
in determining the emergency severity, the processor is configured to compare the set of biophysical data to the medical history or the set of emergency-triggering thresholds.

14. The emergency evacuation system of claim 11, further comprising:
a set of motion detectors disposed in or on the vehicle, the set of motion detectors comprising one or more of a speedometer, a global positioning device, a video camera, and a proximity sensor,
wherein the motion data comprises one or more of a speed of the vehicle, a moving direction of the vehicle, and a distance between the vehicle and a nearby object, and
wherein, in receiving the motion data of the vehicle, the processor is configured to receive the motion data from the set of motion detectors.

15. The emergency evacuation system of claim 11, further comprising:
a user interface configured to receive a human input from an occupant of the vehicle,
wherein, in determining the emergency severity, the processor is further configured to determine the emergency severity based on the human input.

16. The emergency evacuation system of claim 11, wherein:
in executing an autonomous-driving mode having a high autonomous-driving level, the processor is configured to drive the vehicle autonomously to an emergency room, a hospital, an ambulance, or an emergency medical service (EMS) vehicle.

17. The emergency evacuation system of claim 11, wherein:
in executing an autonomous-driving mode having a middle autonomous-driving level, the processor is configured to drive the vehicle autonomously to a safe location in a vicinity of the vehicle, the safe location comprising a side of a road, a shoulder of the road, or a parking lot by the road, and
in executing an autonomous-driving mode having a low autonomous-driving level, the processor is configured to reduce a speed of the vehicle autonomously until the vehicle fully stops.

18. A method, comprising:
receiving, by a processor, wellness data of a driver driving a vehicle in traffic;

determining, by the processor, an emergency severity based on the wellness data;

determining, by the processor, an evacuation plan based on the emergency severity and an autonomous-driving classification of the vehicle; and executing, by the processor, the evacuation plan such that the vehicle and the driver are evacuated from the traffic with autonomous driving, wherein the evacuation plan comprises a set of autonomous-driving modes allowed by the autonomous-driving classification of the vehicle, each of the autonomous-driving modes having a respectively different autonomous-driving level, and wherein the executing of the evacuation plan comprises attempting to execute the set of autonomous-driving modes in a descending order of the autonomous-driving levels until one of the set of autonomous-driving modes is executed successfully.

19. The method of claim 18, wherein:

the receiving of the wellness data of the driver comprises receiving the wellness data from a set of sensors disposed in or on the vehicle, or worn by the driver, the set of sensors comprises one or more of a heart rate sensor, a blood pressure sensor, a thermometer, a respiratory rate monitor, a video camera, and an infrared image sensor, the wellness data comprises a set of biophysical data comprising one or more of a heart rate reading, a blood pressure reading, a body temperature reading, a respiration reading, a body movement, an eye movement, and a facial distortion the wellness data further comprises a medical history, a set of emergency-triggering thresholds, or both, associated with the driver, and the determining of the emergency severity comprises comparing the set of biophysical data to the medical history or the set of emergency-triggering thresholds.

* * * * *